(12) United States Patent
Lange et al.

(10) Patent No.: US 8,317,833 B2
(45) Date of Patent: Nov. 27, 2012

(54) ELONGATED STABILIZATION MEMBER AND BONE ANCHOR USEFUL IN BONE AND ESPECIALLY SPINAL REPAIR PROCESSES

(75) Inventors: Robert Lange, Paris (FR); Andreas Bihl, Schlieren (CH); Steve Olson, Knoxville, TN (US); David Luensmann, Westminster, CO (US)

(73) Assignee: coLigne AG, Zurich (CH)

( * ) Notice: Subject to any disclaimer, the term of this patent is extended or adjusted under 35 U.S.C. 154(b) by 1006 days.

(21) Appl. No.: 12/053,870

(22) Filed: Mar. 24, 2008

(65) Prior Publication Data
US 2008/0262548 A1    Oct. 23, 2008

Related U.S. Application Data

(60) Provisional application No. 60/907,175, filed on Mar. 23, 2007.

(51) Int. Cl.
*A61B 17/70* (2006.01)
(52) U.S. Cl. ...................................................... 606/256
(58) Field of Classification Search ........... 606/246–279
See application file for complete search history.

(56) References Cited

U.S. PATENT DOCUMENTS

| | | | |
|---|---|---|---|
| 4,743,260 A | | 5/1988 | Burton |
| 5,415,661 A | * | 5/1995 | Holmes .......................... 606/255 |
| 2004/0236327 A1 | * | 11/2004 | Paul et al. ....................... 606/61 |
| 2005/0203513 A1 | | 9/2005 | Jahng et al. |
| 2006/0041259 A1 | | 2/2006 | Paul et al. |
| 2007/0005063 A1 | | 1/2007 | Bruneau et al. |
| 2007/0016190 A1 | | 1/2007 | Martinez et al. |
| 2007/0270821 A1 | * | 11/2007 | Trieu et al. ....................... 606/61 |

FOREIGN PATENT DOCUMENTS

| | | |
|---|---|---|
| EP | 0 706 876 A1 | 4/1996 |
| EP | 1 238 637 A1 | 9/2002 |
| EP | 1 857 065 A1 | 11/2007 |

* cited by examiner

*Primary Examiner* — Alvin Stewart
*Assistant Examiner* — Summer Kostelnik
(74) *Attorney, Agent, or Firm* — Browdy and Neimark, PLLC

(57) ABSTRACT

The elongated stabilization member comprises a composite rod (R) having a uniform cross-section essentially throughout its length. The rod (R) has at least first and second segments (A, B, C) each of which has a different modulus of elasticity. Preferably the rod (R) is comprised of plastic with carbon fibers disposed therein and said first and second segments (A, B, C) have different orientation densities of fibers or lengths to provide said different moduli of elasticity.

22 Claims, 11 Drawing Sheets

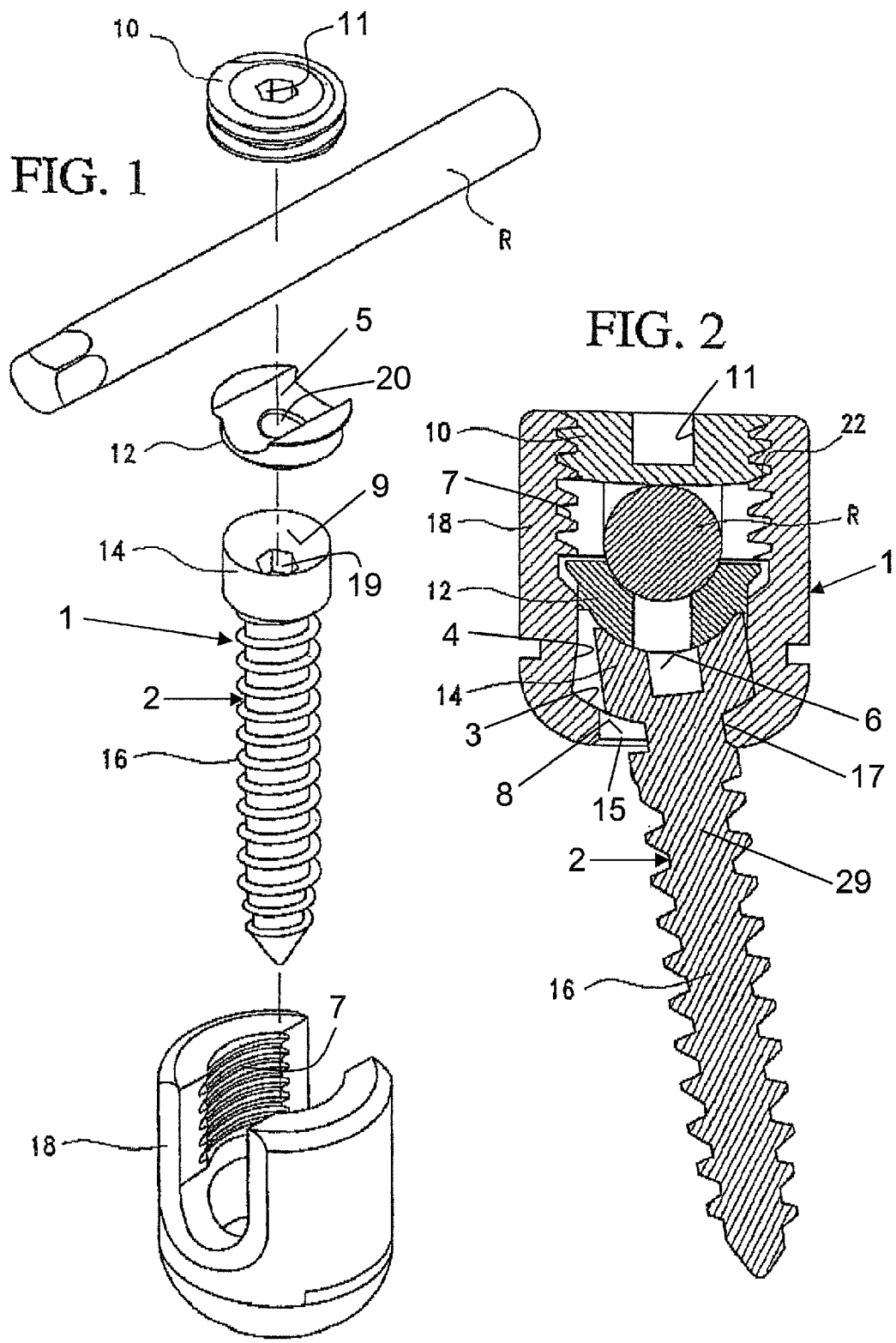

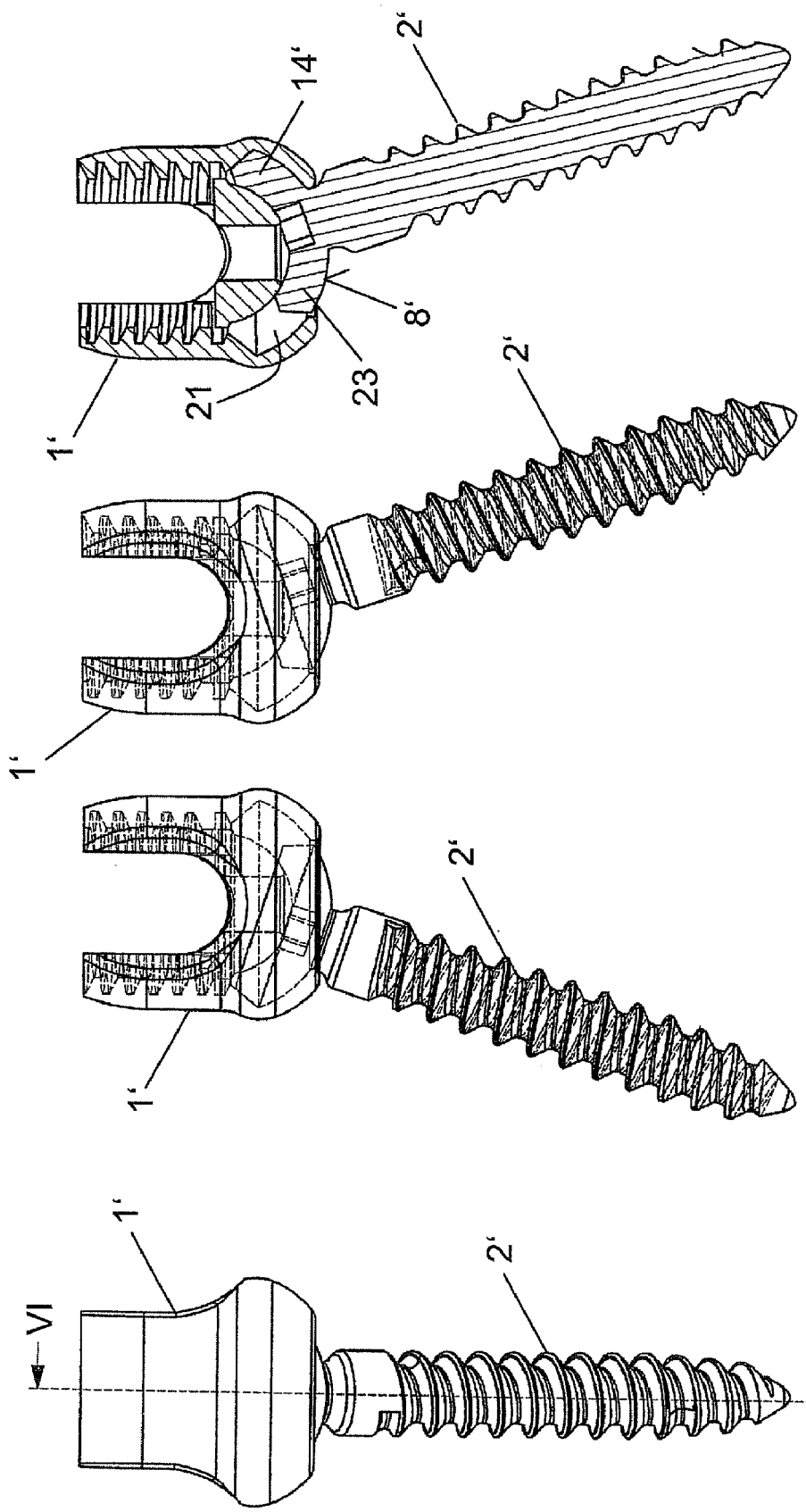

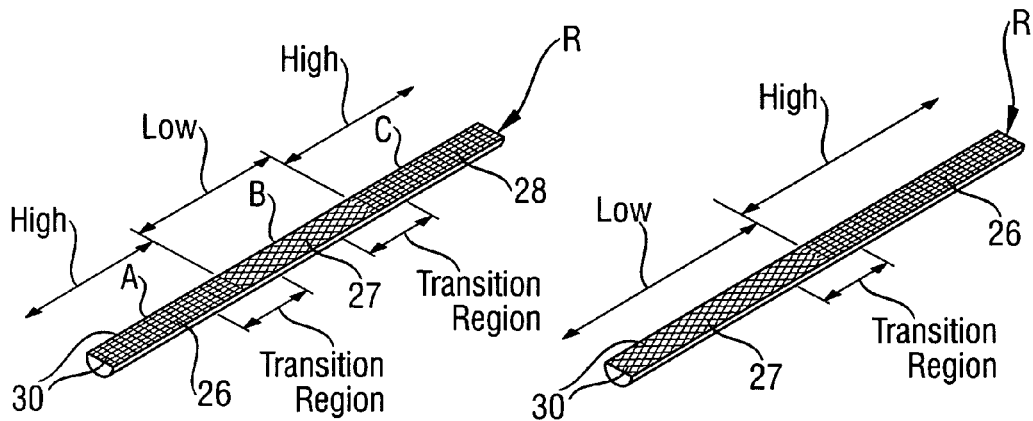
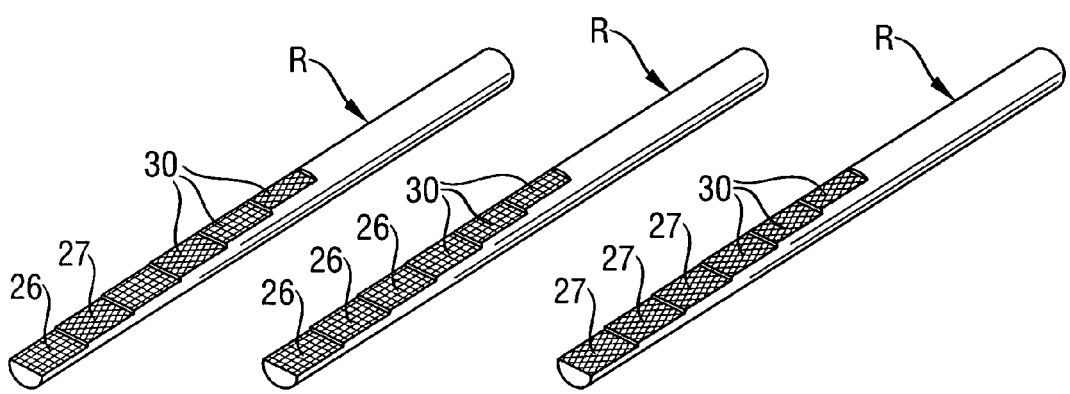
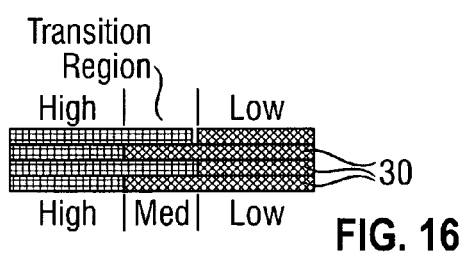
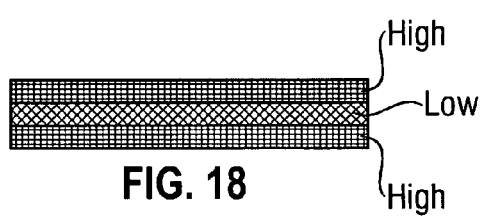
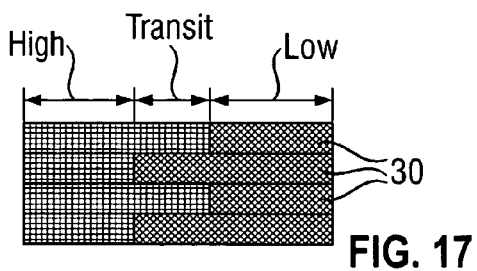
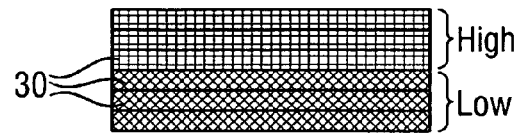

ELONGATED STABILIZATION MEMBER AND BONE ANCHOR USEFUL IN BONE AND ESPECIALLY SPINAL REPAIR PROCESSES

The present invention relates to an elongated stabilization members and a bone interface anchor for use with such elongated stabilization members.

BACKGROUND

In prior art EP-A-0 755 228 discloses a stabilization member and a bone interface anchor, wherein the stabilization member is a rod. The anchor has a retaining member which has a channel which is adapted to receive said rod and compression means for compressively securing the stabilization member in the retaining member with the compression means. With a downward compression force can be applied on the rod to bias it against a screw head.

EP-A-0 934 027 describes a multi-axial bone crew assembly, which comprises a crown member for engagement with the bone crew. With a compression member a rod is pressed against said crown member and said crown member is pressed against the head of a bone screw.

EP-A-1 240 875 discloses a spinal osteosynthesis member which has inside a U-shaped opening of the connector a ring cable of coming into contact with the head of a bone screw. A rod is inserted into the U-shaped opening and biased with a locking member against said ring to the head of a pedicle screw.

Similar polyaxial fixing systems are known from WO 02/02024, WO 2005/016161 and WO 2006/083773.

SUMMARY OF THE INVENTION

The invention relates to an elongated stabilization member useful in bone and especially spinal repair processes. The elongated stabilization member comprises a composite rod having a uniform cross-section essentially throughout its length and said rod having first and second segments each of which has a different modulus of elasticity. The stabilization member of the present invention has the advantage that I can approach the modular elasticity of bone without any danger of breakage. It further provides limited motion to the connected bones and can fulfill the biomechanical requirement which are needed to increase the muscle as well as the strength of the bones to which the muscles are connected. The rod can have variable stress characteristics throughout its length and a uniform cross-section essentially throughout its length. The uniform cross-section makes it possible to use the rod with almost any of the standard connectors. As the rod is made from composite it has the advantage of enhanced imaging throughout the length of the rod. The invention is especially useful for treatment of spinal bone cancer which requires radiation treatment in addition to stabilization, wherein it facilitates proper dosage of radiation adjoint to the implant.

DESCRIPTION OF THE FIGURES

FIG. 1 is an exploded perspective view of the components of the bone interface anchor and the elongated stabilization member according to one exemplary embodiment of the invention, FIG. 2 is a cross-sectional view of the anchor and stabilization member in the assembled state, FIG. 3 is a side view of the anchor according to an alternative embodiment of the invention, FIG. 4 is a partial cross-sectional view of the anchor as shown in FIG. 3, FIG. 5 is another partial cross-sectional view of the anchor as shown in FIG. 3, FIG. 6 is a cross-section of the anchor taken along line VI-VI shown in FIG. 3.

DESCRIPTION OF THE PREFERRED EMBODIMENT

Figures 7, 8, 9, 10:
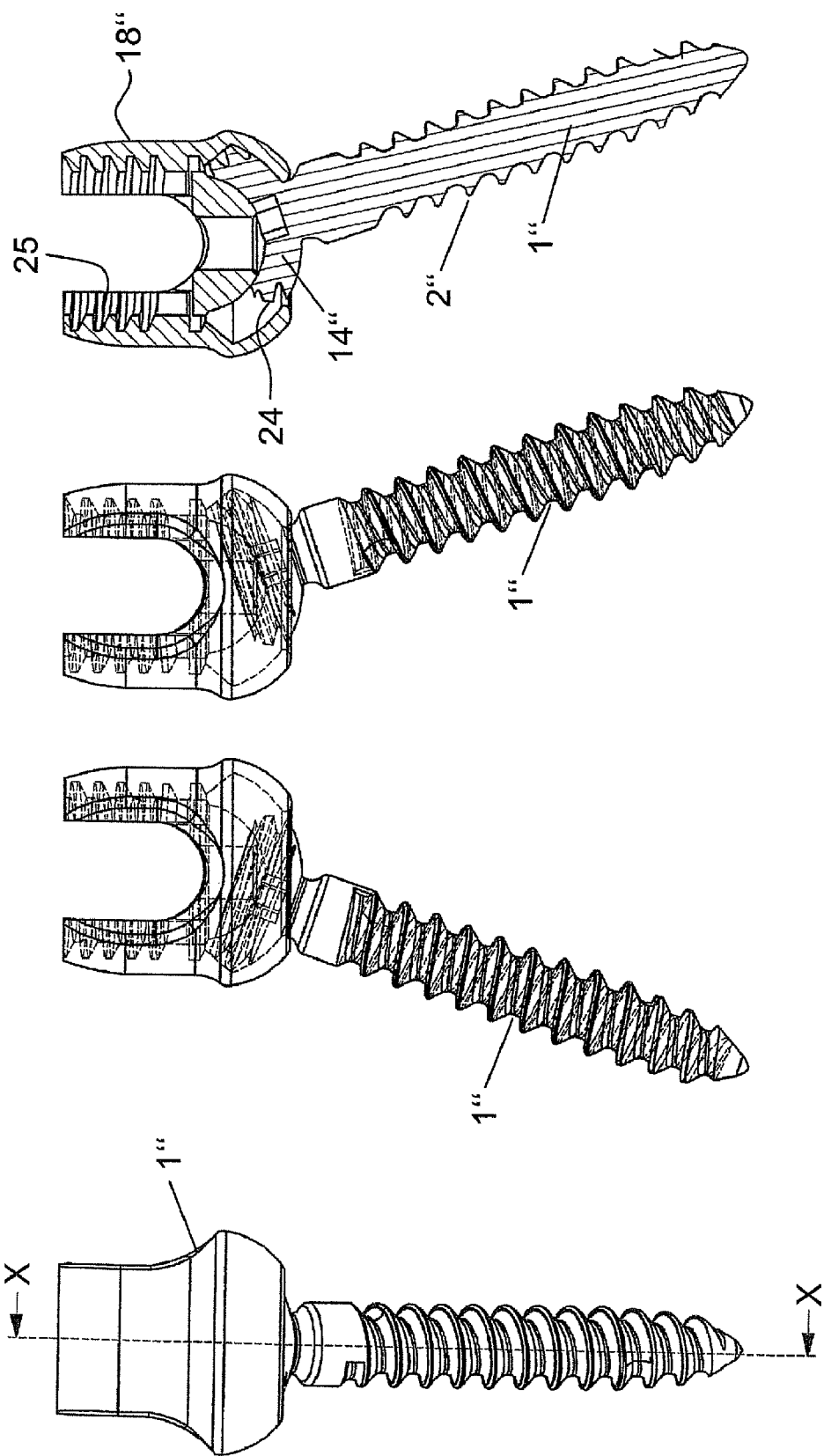
FIG. 7 is a side view of the anchor according to an alternative embodiment of the invention.
FIG. 8 is a partial cross-sectional view of the anchor as shown in FIG. 7.
FIG. 9 is another partial cross-sectional view of the anchor as shown in FIG. 7.
FIG. 10 is a cross-section of the anchor taken along line X-X shown in FIG. 7, FIG. 11-19 cross-sections of the elongated stabilization member.

FIGS. 1 and 2 show the components of the bone interface anchor 1 and a stabilization member, especially a rod R which, as shown in the drawings, is straight throughout its length, is clamped as shown in FIG. 2. The components of the anchor 1 include a compression member, especially a nut 10, a receptor 18, a crown member 12 and a bone screw 2. The nut 10 is disposed within a bore 4 of the receptor 18 for engagement with the rod R and bias the rod R against a crown member 12 which engages a head 14 of the screw 2 at a concave surface 9 (FIG. 1). The invention is disclosed with a bone screw, but other bone fixation members could be used instead.

The receptor 18 has a threaded portion 7 configured to engage the nut 10 which has a corresponding outer thread 22. The nut 10 also includes a tool recess 11 which can be a hex recess.

The rod R is locked between the nut 10 and the crown member 12. The upper side of the crown member 12 has a groove 5 which engages the rod R. This groove 5 increases the contact surface to the rod R and therefore the crown member 12 can be better propagate forces. The rod R is gripped tighter and with less deformation. The rod R as illustrated in FIG. 1 has a round cross section. It is envisioned that the rod R can have other cross sections, wherein the groove is made correspondingly.

The crown member 12 has a bottom surface 6 which is vex and especially spherical. This surface 6 engages the concave surface 9 of the screw head 14 which is preferably spherical as well. The surfaces 6 and 9 are glide and lock surfaces. Further glide and lock surfaces are a convex surface at the bottom of the screw head 14 and a concave surface 3 at the bottom of the bore 4. Within the concave surface 3 there is an opening 15 for receiving the screw 2. The screw 2 has a shank 29 with a recess 17. The diameter of the shank 29 at the recess 17 is smaller than the diameter of the opening 15. The opening 15 can be round or oval.

When the nut 10 is not tightened, the receptor 18 is pivotable with respect to the longitudinal axis of the screw 2. In order to fix the rod R, the surgeon tightens the nut 10. The pressure between the nut 10, the rod R, the crown member 12, the screw head 14 and the bottom of the receptor 18 secures the assembly regardless of the angle between the screw 2 and the receptor 18.

The fixed rod R not only connects the vertebra to be fused, its well exerts stable pressure upon the crown member 12. In order to have enough friction between the surface 3 of the receptor 18, the crown member 12 is made with a comparatively large mass. Furthermore, the crown member 12 has the shape of a saddle and engages the rod R with a comparatively large surface. The crown member 12 can therefore without much loss propagate the force to the screw head 14 and therefore effects a solid fixation regardless of the angle between the screw 2 and the receptor 18. It has been shown that the anchor is especially suitable for a rod R made from a composite material, and especially a composite material with carbon fibers disposed therein. When the rod R is made from a composite material, there is almost no friction between the nut 10 and the rod R. Therefore, almost all of the pressure from the torque exerted on the nut 10 is upon the rod R and upon the threads of the anchor. When the rod R is made of titanium, there is considerably more friction between the nut 10 and the rod R and this friction absorbs part of the torque and part of the pressure, placing less stress on the threads and less pressure on the rod R.

The rod R is especially suitable in combination with the anchor, when it contains fibers 30 and especially carbon fibers as illustrate in FIGS. 11 to 19. These fibers 30 not only affect stiffness between vertebrae, but at the same time the fibers 30 propagate the pressure from the nut 10 to the crown member 12. The fibers 30 make the crown member 12 work biomechanically, because they transmit the force to the crown member 12. The rod 10 is preferably anisotropic and has both the ability to exert a steady pressure and a control motion between fused vertebral bones.

The FIGS. 3 to 6 disclose an anchor 1' which has a screw 2', provided with a collar 23 disposed within a recess 21. The collar 23 is provided with a comparatively large surface.

FIGS. 7 to 10 show an alternative anchor 1" which has a thread 24 which is made corresponding to the thread 25 of the receptor 18".

The rods R as illustrated in FIG. 11 has a first segment A, a second segment B and a third segment C which have different moduli of elasticity. The modulus of elasticity in the second segment B is lower than in the segments A and C. The rod R may have more than three segments or only two segments as illustrated in FIG. 12.

The reinforcement of the rod R with fibers 30 helps to eliminate creep and spreads the load more evenly over a larger area. With the different moduli of elasticity it is possible to control motion between if used vertebral bones. The rod R can provide limited motion to the fused bones which helps to increase the muscle as well the strength of the bones to which the muscles are connected.

The sections A and C as shown in FIG. 11 contain plies 26, 27 and 28 made from fibers 30 and especially carbon fibers. The fibers 30 of the ply 26 and ply 28 are mainly parallel to the longitudinal direction of the rod R, whereas the fibers of the ply 27 are crossed and oblique to the longitudinal direction of the rod R. The plies 26 and 28 effect therefore a higher stiffness than the ply 27.

The plies 26, 27 and 28 can be arranged in a sandwich design as illustrated in FIGS. 13 to 19. FIG. 13 shows a segment with plies 26 and 27 which are parallel to each other and which are disposed alternatively. The segment as shown in FIG. 13 has therefore a stiffness which is between the high stiffness of segment A and the lower stiffness of segment B.

FIG. 14 shows a segment made with plies 26 and has therefore a comparatively high stiffness, whereas the segment shown in FIG. 15 is made with segments 27 and has therefore a comparatively low stiffness.

FIGS. 16 to 19 show other possibilities to make segments with different moduli of elasticity. To provide different moduli of elasticity, segments can have different densities of fibers and/or fibers of different lengths.

FIGS. 20 to 24 disclose a transverse connector 31 comprising a rod 32 made from a carbon composite material, two stiffener 33 and 34 and two connectors 35. The rod 32 is clamped at its ends with nuts 37 which exert a pressure force on the stiffness 33 and 34 as well as on the rod 32. The connectors 35 could be the tulip anchors as shown in FIGS. 1 to 10 and the rod 32 could be a rod R as disclosed in FIGS. 11 to 19.

Figure 20:
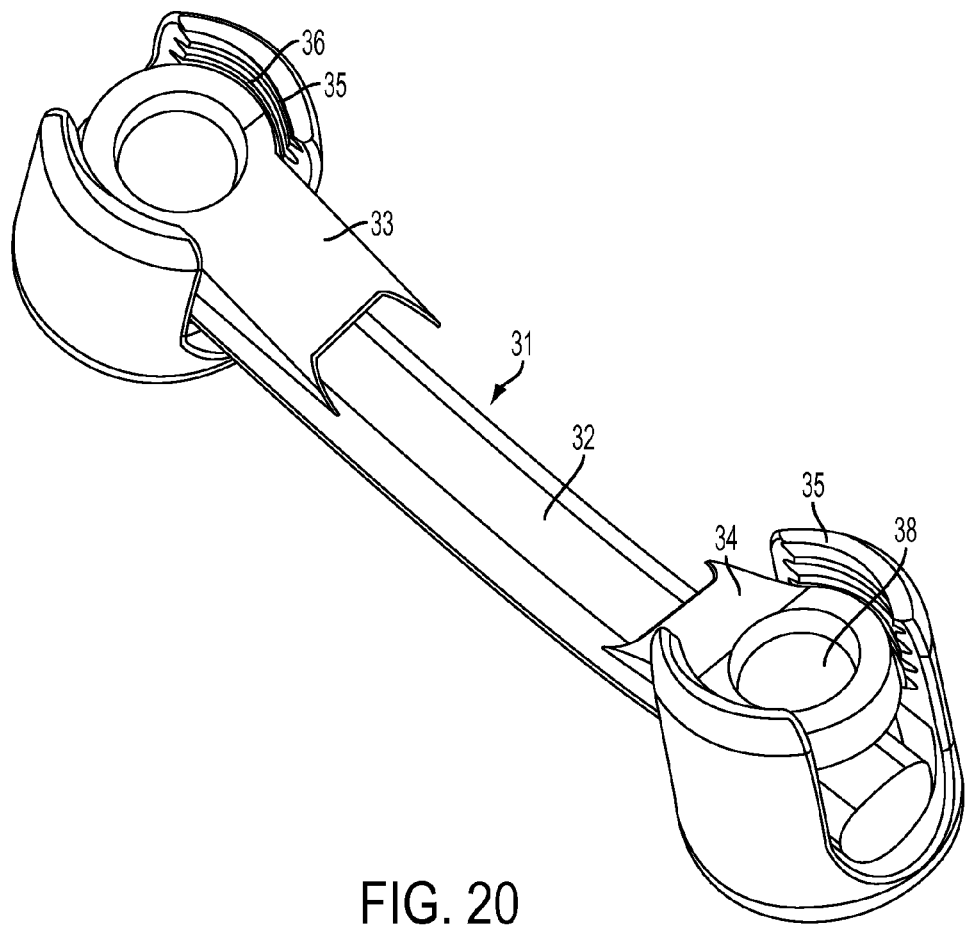
FIG. 20 is a perspective view of a transverse connector.
Figure 21:
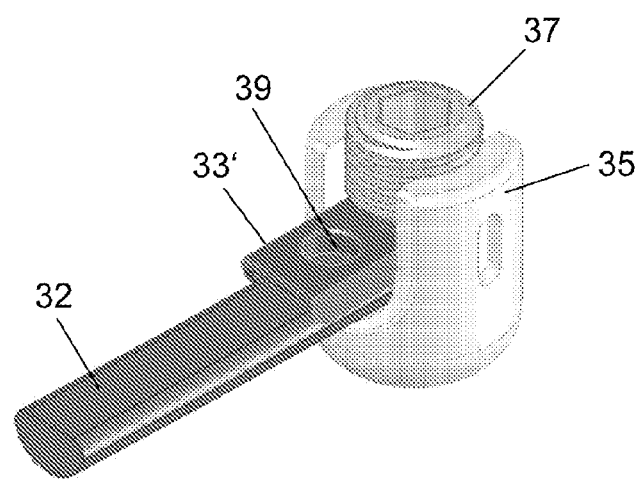
FIG. 21 is a perspective view of a part of a transverse connector
Figure 22:
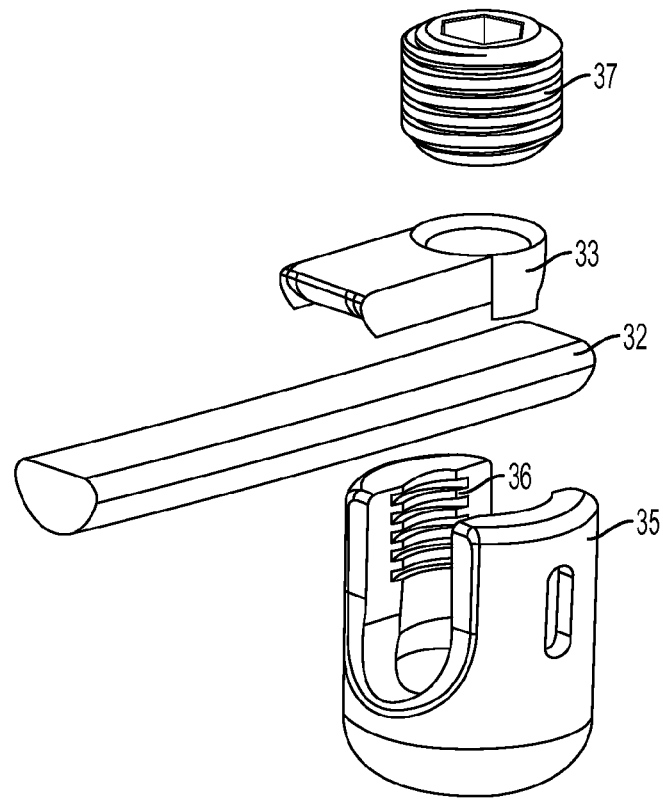
FIG. 22 is an exploded perspective view of the part shown in FIG. 21.
Figure 23:
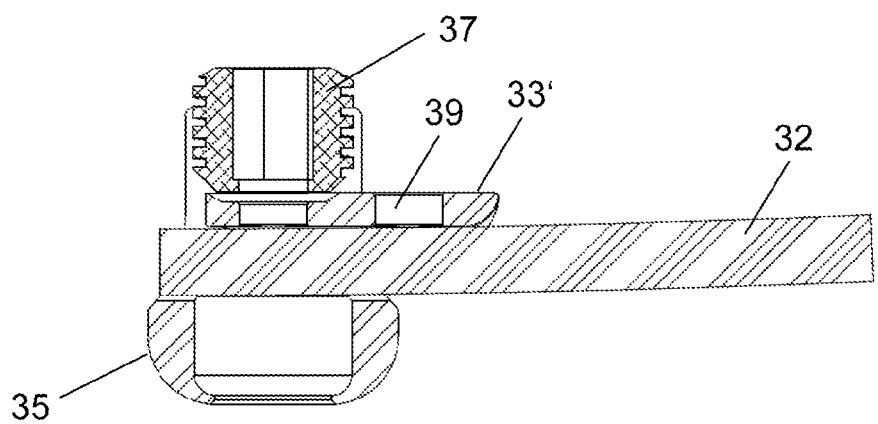
FIG. 23 is a cross-sectional view of the part shown in FIG. 23.
Figure 24:
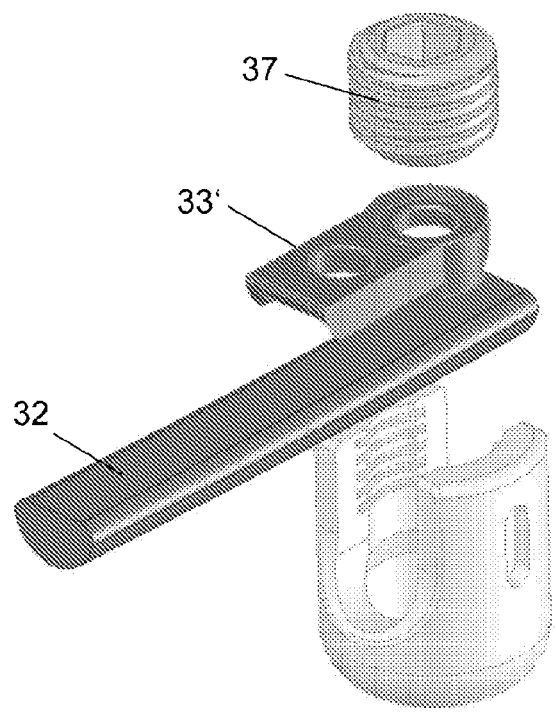
FIG. 24 is another exploded perspective view of the part shown in FIG. 21.
Figure 25:
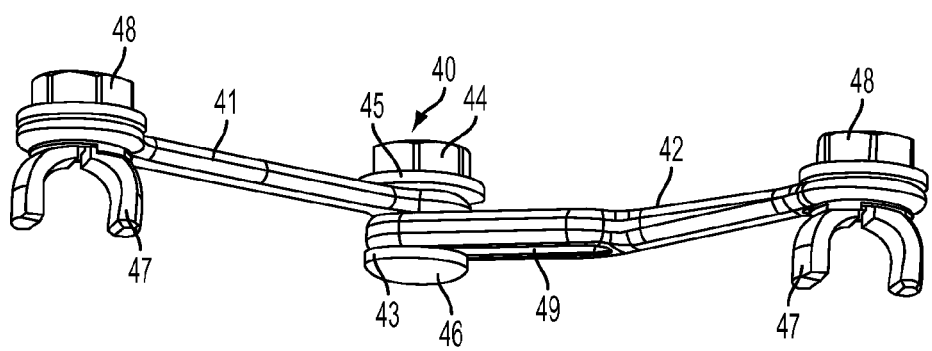
FIG. 25 is a perspective view of a transverse connector having two longitudinal elements connected via an articulation.
Figure 26:
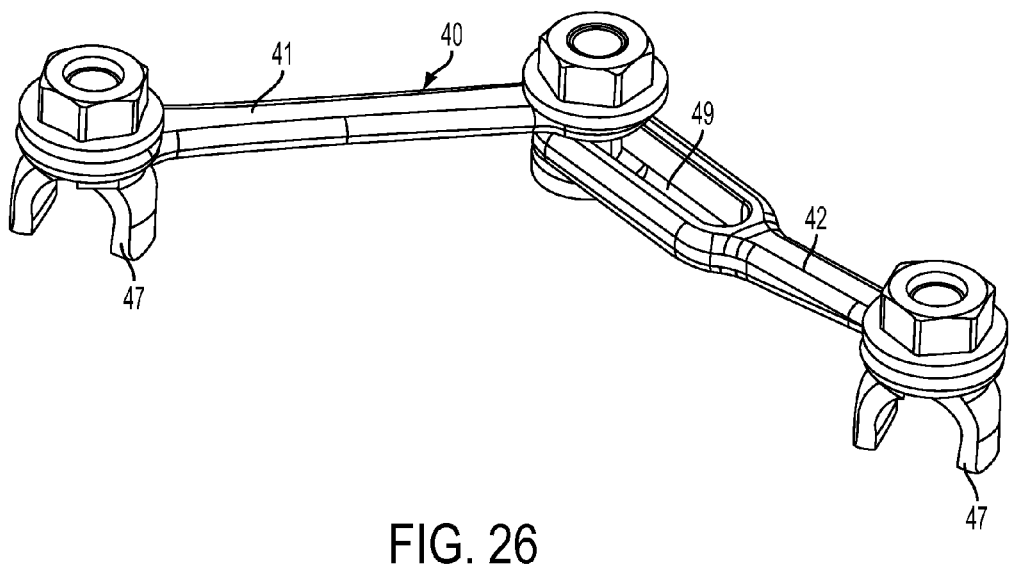
FIG. 26 is another perspective view of the transverse connector shown in FIG. 25.
Figure 27:
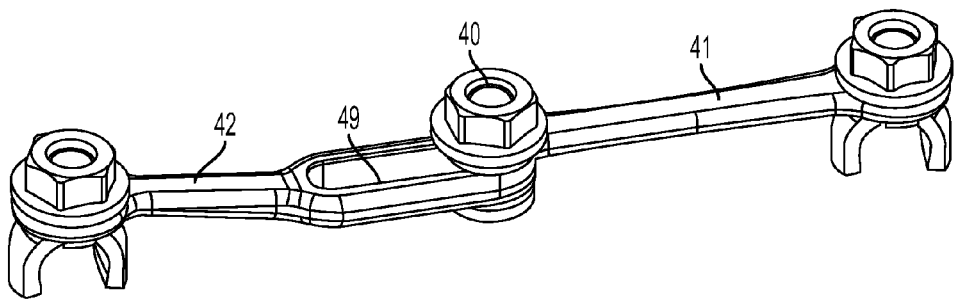
FIG. 27 is another perspective view of the transverse connector shown in FIG. 25.
Figure 28:
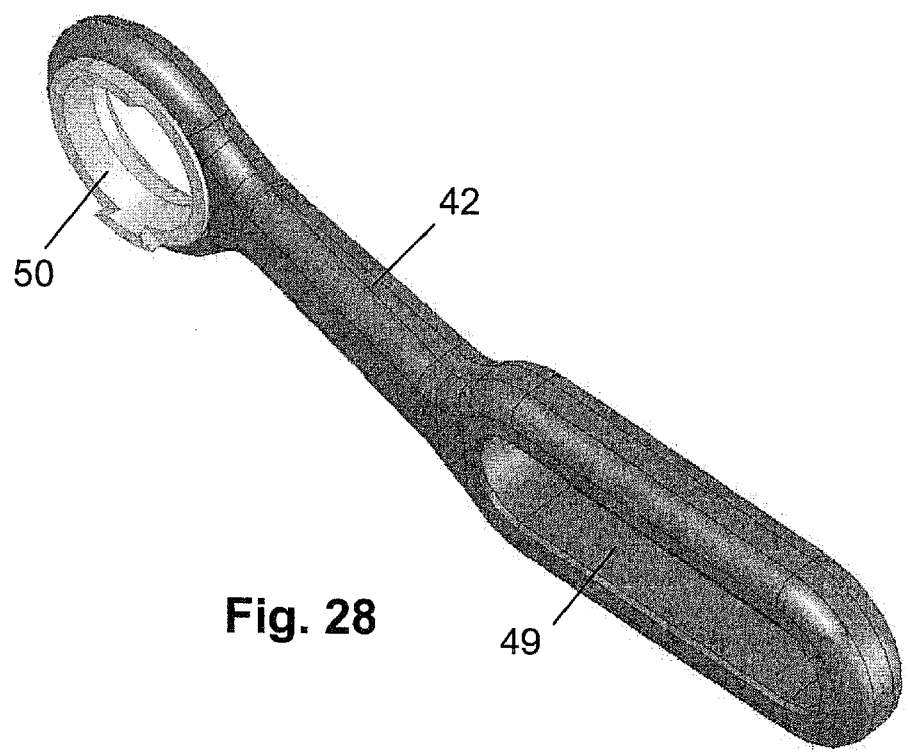
FIG. 28 is a perspective view of a part of the connector shown in FIG. 25.
Figure 29:
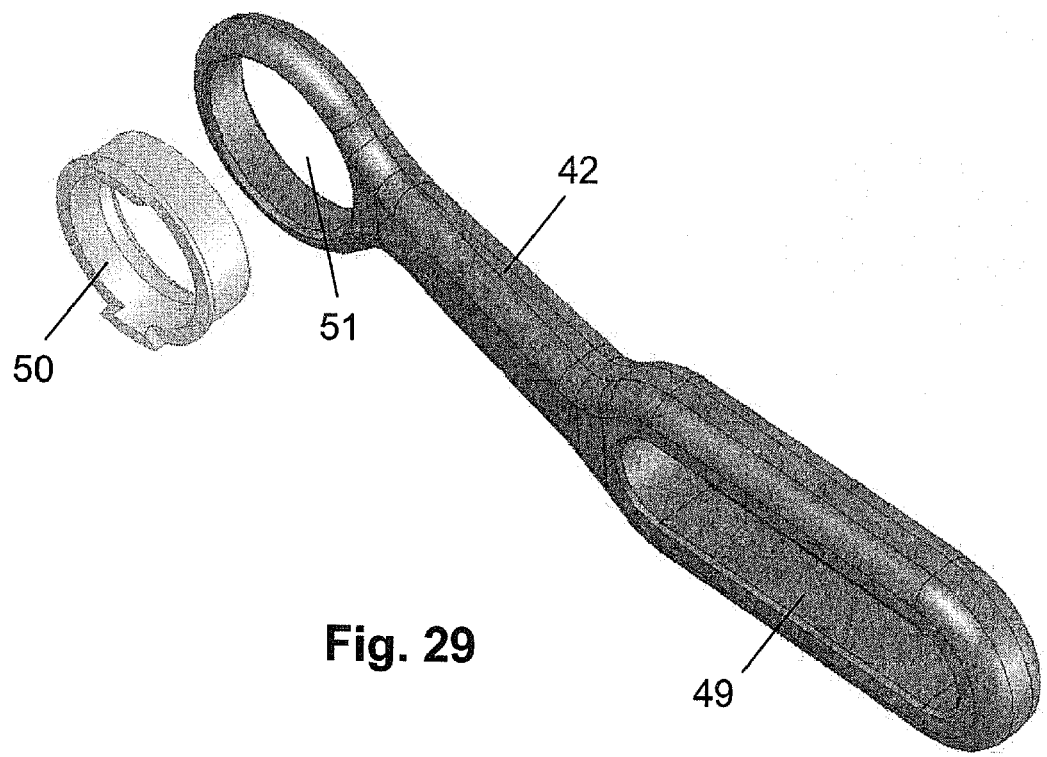
FIG. 29 is an exploded perspective view of the part shown in FIG. 28.
Figure 30:
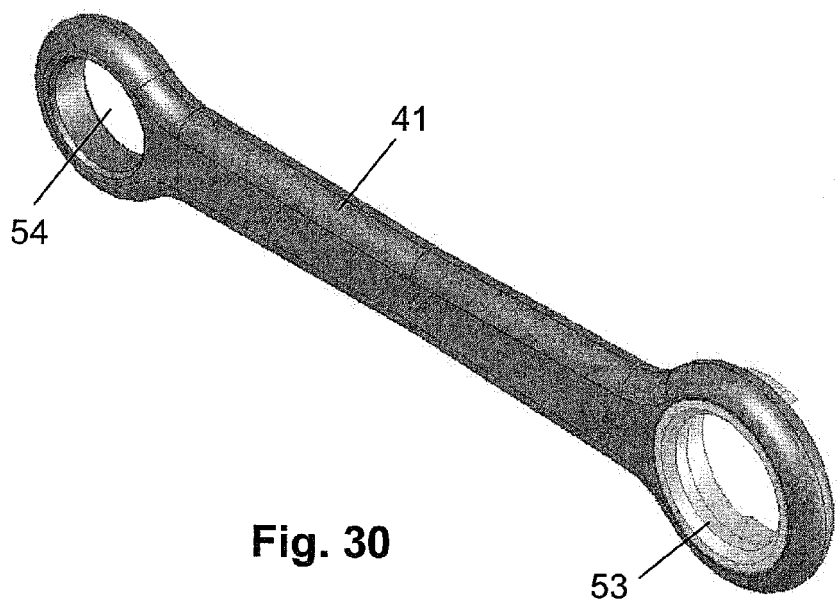
FIG. 30 is a perspective view of another part of the connector shown in FIG. 25.
Figure 31:
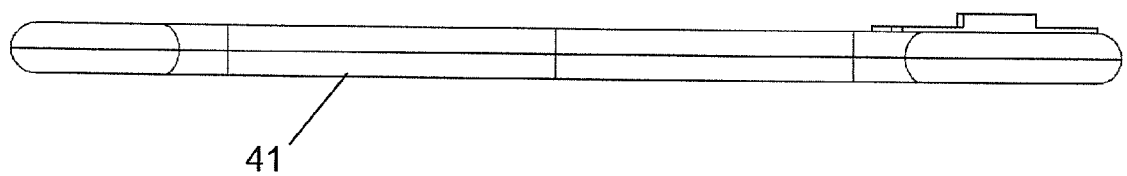
FIG. 31 is a side view of the part shown in FIG. 30.
Figure 32:
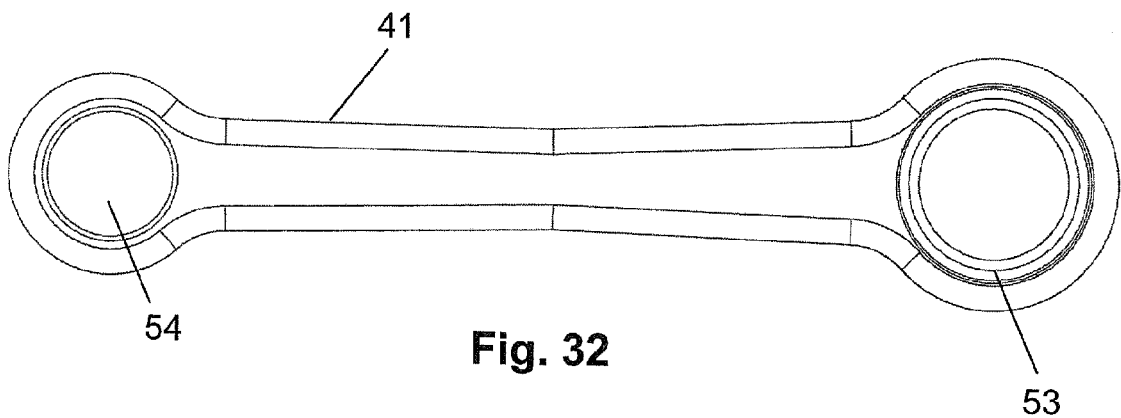
FIG. 32 is another view of the part shown in FIG. 30
Figure 33:
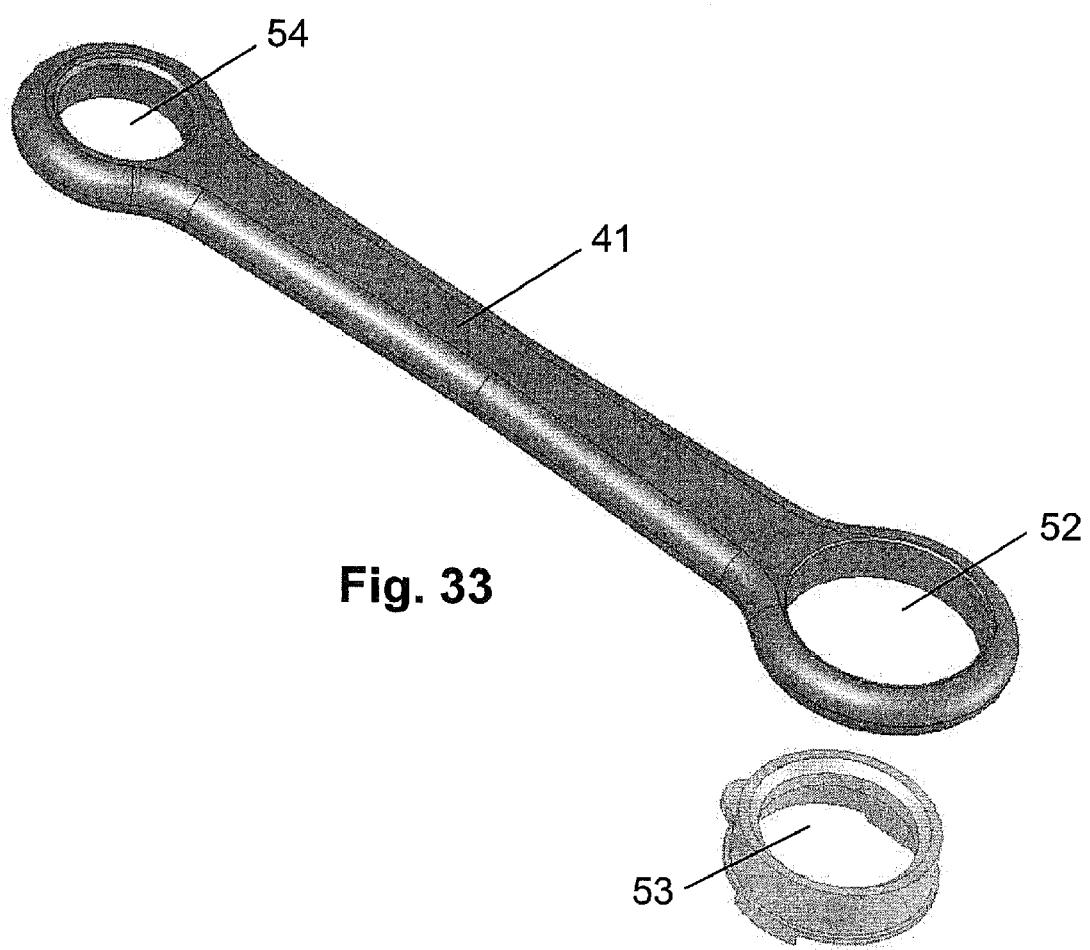
FIG. 33 is an exploded perspective view of the part shown in FIG. 30.

The stiffeners 33 and 34 are made from a stable metal preferably of titanium. As shown in FIG. 20, the stiffeners 33 and 34 can be different, for example differently long. The transverse connector 31 can for example have a higher stiffness in the area of the stiffener 33 than in the area of the stiffener 34, as the stiffener 33 is longer than the stiffener 34. The stiffener 33' as shown in FIGS. 21 to 24 has a hole 39, which lowers the stiffness compared with a stiffener without this hole.

The rod 32 preferably contains carbon fibers 30 as shown in FIGS. 11 to 19. A part of these fibers have a direction which is oblique to the longitudinal direction of the rod 32. These fibers have the effect that they prevent deformation of the rod 32 due to the pressure of the nut 10. The cross-section of the rod 32 does therefore essentially not change when the rod is clamped with a comparatively high pressure. The cross-section even does not change later when the connector is implanted. The same feature relates to the rod R shown in FIGS. 11 to 19.

FIGS. 25 to 33 show a transverse connector 40 comprising a first longitudinal element 41, a second longitudinal element 3, an articulation 43, which connects the elements 41 and 42 and two clamps 47. With the clamps 47 and the nuts 48 the transverse connector 40 is connected with stabilization rods as shown in FIGS. 1 and 2. The element 42 comprises an oblong hole 49 which allows to vary the angel between the two elements and the distance. Within a hole 51 a ring 50 is pivotably disposed which is made of a metal, for example titanium. The elements 41 and 42 are made of a carbon fiber of a metal, for example titanium. The elements 41 and 42 are made of a carbon fiber composite material. The part 41 is as well made of a composite material and has at its ends a hole 54 and in another hole a pivotable ring 53, made of a metal and especially titanium. The rings 50 and 53 are disposed at the ends where the nuts 48 and clamps are arranged.

| List of reference numbers | |
|---|---|
| 1 | bone interface anchor |
| 2 | screw |
| 3 | surface |
| 4 | bore |
| 5 | groove |
| 6 | surface |
| 7 | thread |
| 8 | surface |
| 9 | surface |
| 10 | compression means |
| 11 | tool recess |
| 12 | crown member |
| 13 | channel |
| 14 | screw head |
| 15 | opening |
| 16 | thread |
| 17 | recess |
| 18 | receptor |
| 19 | tool recess |
| 20 | opening |
| 21 | recess |
| 22 | thread |
| 23 | collar |
| 24 | thread |
| 25 | thread |
| 26 | ply |
| 27 | ply |
| 28 | ply |
| 29 | shank |
| 30 | fibers |
| 31 | transverse connector |
| 32 | longitudinal element (rod) |
| 33 | stiffener |
| 34 | stiffener |
| 35 | connector (anchor) |
| 36 | thread |
| 37 | nut |
| 38 | bore |
| 39 | hole |
| 40 | transverse connector |
| 41 | first longitudinal element |
| 42 | second longitudinal element |
| 43 | articulation |
| 44 | nut |
| 45 | disk |
| 46 | screw |
| 47 | clamp |
| 48 | nut |
| 49 | oblong hole |
| 50 | ring |
| 51 | hole |
| 52 | hole |
| 53 | ring |
| 54 | hole |
| A | segment |
| B | segment |
| C | segment |
| R | rod |

The invention claimed is:

1. An elongated stabilization member useful in bone and especially spinal repair processes comprising:
   a composite rod having a uniform cross-section essentially throughout its length, and
   said rod having at least first and second segments each of which has a different modulus of elasticity,
   wherein said rod is comprised of plastic with carbon fibers disposed therein and said first and second segments have respectively different orientations of fibers to provide said different moduli of elasticity, and
   wherein said first and second segments contain plies made from said fibers and said plies are arranged in a sandwich pattern, are parallel to each other and are disposed alternatively.

2. The stabilization member of claim 1, wherein the ratio direction of fiber to plastic varies along the rod length.

3. The stabilization member of claim 1, wherein said plastic and fibers of said rod will not block imaging rays.

4. The stabilization member of claim 1, wherein said rod is comprised with carbon fibers disposed therein and said first and second segments have different densities of fibers to provide said different moduli of elasticity.

5. The stabilization member of claim 1, wherein said rod is comprises with carbon fibers disposed therein and said first and second segments have fibers of different lengths to provide said different moduli of elasticity.

6. The stabilization member of claim 1, wherein said rod is straight throughout its length.

7. An elongate rod for location approximately parallel to and adjacent to a spine,
   said rod having a uniform cross-section throughout its length and is comprised of fiber reinforced plastic, and
   said rod having moduli of elasticity along its length corresponding to, but less than, the moduli of elasticity of the spine segments closest to said rod segments,
   wherein said rod is comprised of plastic with carbon fibers disposed therein and said first and second segments have respectively different orientations of fibers to provide said different moduli of elasticity; and
   wherein said first and second segments contain plies made from said fibers and said plies are arranged in a sandwich pattern, are parallel to each other and are disposed alternatively.

8. A device for treating a human spine having a series of bone segments comprising:
   a composite rod having a uniform cross-sectional dimension throughout its length,
   said rod comprising a plurality of rod segments each having a different modulus of elasticity,
   first and second anchors adapted to be secured to said rod in spaced relationship to one another, and
   each of said anchors including a screw which is adapted to secure said anchors to spaced spinal bone segments,
   wherein said rod is comprised of plastic with carbon fibers disposed therein and said first and second segments have respectively different orientations of fibers to provide said different moduli of elasticity, and
   wherein said first and second segments contain plies made from said fibers and said plies are arranged in a sandwich pattern, are parallel to each other and are disposed alternatively.

9. The device of claim 8, wherein each of said anchors has a bottom surface facing a spinal bone segment,
   means to slidably receive said screw in said anchors, and lock means to affix said anchors to said rod.

10. The device of claim 9, wherein said anchors, said screws and said lock means are made of a carbon reinforced plastic that will not block imaging rays and facilitate radiation treatment.

11. The device of claim 10, wherein first and second anchors of composite material are adapted to be secured to said rod in spaced relationship to one another and each of said anchors includes a screw adapted to secure said anchors to spaced bone segments of the spine.

12. A device for treating a human spine having a series of bone segments comprising:

a composite rod having a uniform cross-sectional dimension throughout its length,
said rod comprising a plurality of rod segments each having a different modulus of elasticity,
first and second anchors adapted to be secured to said rod in spaced relationship to one another,
each of said anchors including a screw which is adapted to secure said anchors to spaced spinal bone segments,
each of said anchors having a bottom surface facing a spinal bone segment,
means securing said screws to said anchors such that said screws can be variably positioned relative to said anchors, and
lock means to fix said anchors to said rods after positioning,
wherein said rod is comprised of plastic with carbon fibers disposed therein and said first and second segments have respectively different orientations of fibers to provide said different moduli of elasticity, and
wherein said first and second segments contain plies made from said fibers and said plies are arranged in a sandwich pattern, are parallel to each other and are disposed alternatively.

13. A bone interface anchor for use with a composite stabilizer rod said anchor comprising:
a receptor having retaining means for receiving said stabilizer,
a compression assembly for securing said stabilizer within said receptor,
bone fixation screws which secure said anchors relative to bone segments of the human spine,
said receptor having a surface forming a mating cooperation with said screw such that said receptor can be variably positioned relative to said screw,
lock means to fix said screw relative to said receptor, and
said retaining means having a crown member between said stabilizer and the interior of said receptor,
wherein said rod is comprised of plastic with carbon fibers disposed therein and said first and second segments have respectively different orientations of fibers to provide different moduli of elasticity, and
wherein said first and second segments contain plies made from said fibers and said plies are arranged in a sandwich pattern are parallel to each other and are disposed alternatively.

14. The bone interface anchor of claim 13, wherein said composite rod has a uniform cross-section throughout its length, and
said rod having first and second segments each of which as a different modulus of elasticity.

15. The bone interface anchor of claim 14, wherein said first and second segments have different densities of fibers to provide said different moduli of elasticity.

16. The bone interface anchor of claim 14, wherein the ratio density of fiber to plastic varies along the rod length.

17. The bone interface anchor of claim 13, wherein the plastic and fibers of said rod an said anchor will not block imaging rays.

18. An assembly for the stabilization of one or more spinal bone segments, comprising:
first and second anchors,
an elongated composite rod having a uniform cross-section throughout its length,
first and second screws each having enlarged heads received respectively by said first and second screws and said anchors and which secure said anchors to a spinal bone segment,
said anchors having cylindrical side walls with a reduced bottom opening of lesser diameter than said heads which retain said heads in a manner providing limited universal movement of said screws with respect to said anchors,
said anchors each having a reception channel 13 to receive said composite rod,
a crown member disposed between said heads and said rod,
said crown members each having a grove formed therein to receive said rod and space said rod from said heads, and
means to compress said rod against said crowns and said crowns against said heads to fix their relationship to one another after the angular disposition of said screws have been selected,
wherein said rod is comprised of plastic with carbon fibers disposed therein and said first and second segments have respectively different orientations of fiber to provide different moduli of elasticity, and
wherein said first and second segments contain plies made from said fibers and said plies are arranged in a sandwich pattern are parallel to each other and are disposed alternatively.

19. The assembly of claim 18, wherein said composite rod is comprised of plastic with carbon reinforcing fibers disposed therein, the density of said fibers providing selected moduli of elasticity throughout the length by varying fiber density.

20. The assembly of claim 19, wherein the components of said anchors are of reinforced plastic that will not block imaging rays.

21. The assembly of claim 18, wherein the rod contains fibers directed to prevent deformation of the rod due to the pressure of the anchor.

22. A rod useful in bone and especially spinal repair processes, made of plastic with fibers disposed therein, wherein at least a part of the fibers have a direction that is oblique to the length of the rod to prevent expansion of the rod with respect to its cross-section, and
wherein said first and second segments contain plies made from said fibers and said plies are arranged in a sandwich pattern are parallel to each other and are disposed alternatively.

* * * * *